United States Patent [19]

Gante et al.

[11] 4,258,047
[45] Mar. 24, 1981

[54] PYRAZOLE DERIVATIVES, PHARMACEUTICAL FORMULATIONS THEREOF

[75] Inventors: Joachim Gante, Darmstadt-Arheilgen; Hans-Eckart Radunz, Mühltal; Dieter Orth, Darmstadt; Klaus Minck, Ober-Ramstadt; Albrecht Wild, Heppenheim; Michael Klockow, Rossdorf, all of Fed. Rep. of Germany

[73] Assignee: Merck Patent Gesellschaft mit beschrankter Haftung, Darmstadt, Fed. Rep. of Germany

[21] Appl. No.: 122,795

[22] Filed: Feb. 19, 1980

[30] Foreign Application Priority Data

Feb. 19, 1979 [DE] Fed. Rep. of Germany ....... 2906252

[51] Int. Cl.³ ................ A61K 31/495; A61K 31/415; C07D 403/12; C07D 401/12
[52] U.S. Cl. .................... 424/250; 424/267; 424/269; 424/270; 424/272; 544/371; 544/373; 546/211; 546/222; 548/152; 548/200; 548/201; 548/217; 548/237; 548/252; 548/254
[58] Field of Search .............. 544/371; 546/211; 548/152, 211, 200, 201, 217, 237, 254; 424/250, 267, 269, 270, 272

[56] References Cited

U.S. PATENT DOCUMENTS 3,367,936   2/1968   Koppe et al. ............. 544/371
4,113,957   9/1978   Möller et al. ............ 544/371

FOREIGN PATENT DOCUMENTS 477463   10/1969   Switzerland ............. 544/371
1206814  9/1970   United Kingdom ....... 544/371

Primary Examiner—Donald G. Daus
Assistant Examiner—James H. Turnipseed
Attorney, Agent, or Firm—Millen & White

[57] ABSTRACT

Pyrazole derivatives of the formula

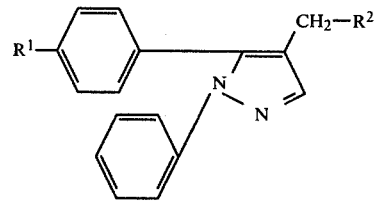

wherein $R^1$ is H or Cl; $R^2$ is 1-methyl-4-piperidyloxycarbonyl, 2-(4-phenylpiperazino)-ethoxycarbonyl, benzoxazol-2-yl, benzthiazol-2-yl, tetrazol-5-yl or 3-$R^3$-4-$R^4$-thiazolidin-2-yl; $R^3$ is H, alkanoyl of 1-7 carbon atoms or benzoyl; and $R^4$ is H or COOH, or a physiologically acceptable salt thereof;
possess valuable pharmacological activities.

8 Claims, No Drawings

PYRAZOLE DERIVATIVES, PHARMACEUTICAL FORMULATIONS THEREOF

The present invention relates to new pyrazole derivatives having pharmacological activity.

SUMMARY OF THE INVENTION

It is an object of one aspect of this invention to provide new compounds having valuable properties, especially those which can be used for the preparation of medicaments.

Upon further study of the specification and appended claims, further objects and advantages of this invention will become apparent to those skilled in the art.

These objects have been achieved by providing pyrazole derivatives of formula I,

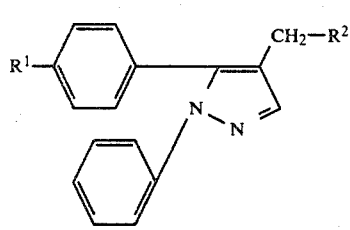

wherein $R^1$ is H or Cl; $R^2$ is 1-methyl-4-piperidyloxycarbonyl, 2-(4-phenylpiperazino)-ethoxycarbonyl, benzoxazol-2-yl, benzthiazol-2-yl, tetrazol-5-yl or 3-$R^3$-4-$R^4$-thiazolidin-2-yl; $R^3$ is H or acyl of 1–7 C atoms; and $R^4$ is H or COOH, and their physiologically acceptable salts.

DETAILED DISCUSSION

The present invention relates to the compounds of formula I and their physiologically acceptable salts.

The radical $R^1$ is preferably Cl. The radical $R^2$ is preferably 1-methyl-4-piperidyloxycarbonyl or 2-(4-phenyl-piperazino)-ethoxycarbonyl. The radicals $R^3$ and $R^4$ are each preferably H. Acyl (in the radical $R^3$) is preferably alkanoyl of 1–7 C atoms or benzoyl and especially acetyl, or also, for example, formyl, propionyl, butyryl, isobutyryl, valeryl, hexanoyl or heptanoyl.

Accordingly, the present invention relates in particular to those compounds of formula I in which at least one of these radicals has one of the preferred meanings indicated above.

A particularly preferred group of compounds comprises those compounds of formula I in which $R^1$ is Cl and $R^2$ is 1-methyl-4-piperidyloxycarbonyl or 2-(4-phenylpiperazino)-ethoxycarbonyl, and their physiologically acceptable salts.

Those compounds of formula I in which the radical $R^2$ is 1-methyl-4-piperidyloxycarbonyl or 3-$R^3$-4-$R^4$-thiazolidin-2-yl possess one or two asymmetric carbon atoms. They can therefore be in the form of racemates or, if several asymmetric carbon atoms are present, also in the form of mixtures of several racemates and also in diverse optically active forms. Formula I includes all of these racemic and optically active forms as well as their mixtures.

The present invention also relates to a process for the preparation of the pyrazole derivatives of formula I and of their physiologically acceptable salts, comprising (a) reacting a compound of formula II

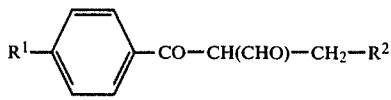

in which $R^1$ and $R^2$ are as defined above, or one of its reactive derivatives, with phenylhydrazine or with one of its salts, or (b) in order to prepare a compound of formula I in which $R^2$ is 1-methyl-4-piperidyloxycarbonyl, 2-(4-phenylpiperazino)-ethoxycarbonyl, benzoxazol-2-yl or benzthiazol-2-yl, reacting a carboxylic acid of formula III

 R—COOH III in which R is the group

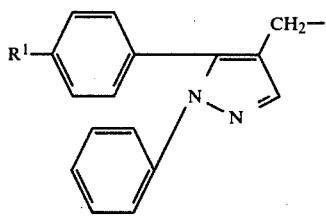

and $R^1$ is as defined above, or one of its reactive derivatives, with a compound of formula IV

 H—$R^5$ IV in which $R^5$ is 1-methyl-4-piperidyloxy, 2-(4-phenylpiperazino)-ethoxy, 2-aminophenoxy or 2-aminophenylthio, or one of its reactive derivatives, or (c) in order to prepare a compound of formula I in which $R^2$ is tetrazol-5-yl, reacting a nitrile of formula V

 R—CN V in which R is as defined above, or one of its reactive derivatives, with hydrazoic acid or one of its salts, or (d) reacting an amidrazone of formula VI

 R—C(=NH)—NHNH$_2$ VI in which R is as defined above, with nitrous acid or one of its salts, or (e) in order to prepare a compound of formula I in which $R^2$ is benzthiazol-2-yl or 3-$R^3$-4-$R^4$-thiazolidin-2-yl, reacting an aldehyde of formula VII

 R—CHO VII in which R is as defined above, or one of its reactive derivatives, with a compound of formula VIII

 $R^6$—SH VIII in which $R^6$ is o—$H_2N$—$C_6H_4$— or NH$R^3$—CH$R^4$—CH$_2$— and $R^3$ and $R^4$ are as defined above, or one of its reactive derivatives, the reaction being carried out in the presence of an oxidizing agent if $R^6$ is a o—$H_2$N—$C_6H_4$— group, or (f) in order to prepare a compound of formula I in which $R^2$ is 3—$R^3$—4—$R^4$—thiazolidin-2-yl and $R^3$ is an acyl group of 1–7 C atoms, treating a compound of formula I in which $R^2$ is 3—$R^3$—4—$R^4$—thiazolidin-2-yl and $R^3$ is H with an acylating agent, and/or (g) if desired, converting a base or acid of formula I to one of its physiologically acceptable salts by treatment with an acid or base, respectively.

In other respects, the compounds of formula I are prepared by methods which are in themselves known, such as are described in the literature (for example in the standard works such as Houben-Weyl, Methoden der Organischen Chemie (Methods of Organic Chemistry), Georg-Thieme-Verlag, Stuttgart; and Organic Reactions, John Wiley & Sons, Inc., New York), and in particular under reaction conditions which are known and suitable for the mentioned reactions. It is also possible to make use of variants which are in themselves known and are not mentioned in more detail here.

If desired, the starting materials can also be formed in situ, in such a way that they are not isolated from the reaction mixture but are immediately further reacted to yield the compounds of formula I.

The starting materials of formula II are new. They are obtainable, for example, by formylation of ketones of the formula p—$R^1$—$C_6H_4$—CO—$CH_2$—$CH_2$—$R^2$, for example with ethyl formate; these ketones, in turn, are accessible by various routes, for example analogously to the methods described further below, for example (if $R^2=R^5$) by reacting 3-benzoyl- or 3-p-chlorobenzoylpropionic acid, or a reactive derivative thereof, with a compound of the formula H—$R^5$ (IV) or one of its reactive derivatives, or (if $R^2$=tetrazol-5-yl) by reacting a nitrile of the mentioned keto-acids, or of a reactive derivative thereof, with hydrazoic acid or one of its salts, or (if $R^2$=benzthiazol-2-yl or 3—$R^3$—4—$R^4$—thiazolidin-2-yl) by reacting a corresponding keto-aldehyde, or a reactive derivative thereof, with a compound of the formula $R^6$—SH (VIII).

Suitable reactive derivatives of the compounds of formula II are preferably the corresponding enol-ethers, enol-esters or enamines, which are obtainable in conventional manner from the compounds II. The dimethylaminoenamines of the formula p—$R^1$—$C_6H_4$—CO—C($CH_2$—$R^2$)=CH—N($CH_3$)$_2$ are particularly preferred; these are preferably obtainable by reaction of the above-mentioned ketones of the formula p—$R^1$—$C_6H_4$—CO—$CH_2$—$CH_2$—$R^2$ with dimethylformamide dimethyl acetal in the presence of acetic acid.

The reaction of the compounds of formula II, or of their reactive derivatives, with phenylhydrazine, or its salts, can be carried out without solvents or in an inert solvent, at temperatures of approximately 0° to about 160° C. and preferably of 70°–120° C. Suitable solvents include, for example, alcohols, e.g., methanol, ethanol or n-butanol, hydrocarbons, e.g., benzene, toluene or xylene, chlorinated hydrocarbons, e.g., chlorobenzene, ethers, e.g., diethyl ether, tetrahydrofuran (THF) or dioxane, ethylene glycol mono- or di-alkyl ethers or diethylene glycol mono- or di-alkyl ethers, e.g., methylglycol or ethylglycol, aliphatic carboxylic acids, e.g., acetic acid, amides, e.g., dimethylformamide (DMF) or N-methylpyrrolidone, and sulfoxides, e.g., dimethylsulfoxide. The reaction times are as a rule approximately 30 minutes to 8 hours. The reaction is preferably carried out in an approximately neutral medium, for example with the addition of acetic acid or, if a salt of phenylhydrazine is used, with the addition of sodium acetate.

Compounds of formula I in which $R^2=R^5$ can preferably be prepared by reacting carboxylic acids of formula III, or their reactive derivatives, with compounds of formula IV, or their reactive derivatives. Suitable reactive derivatives of III include, for example, the corresponding acid halides, especially the chlorides, and also the esters, especially alkyl esters in which the alkyl group contains 1–4 C atoms, and also nitriles, amides, anhydrides or imido-esters. Suitable functional derivatives of the alcohols or phenols of formula IV include in particular the corresponding metal alcoholates and metal phenolates, especially the alkali metal alcoholates or alkali metal phenolates. The starting materials III and IV are known and their reactive derivatives can be obtained easily from these compounds by methods which are in themselves known.

An esterification reaction of the carboxylic acids III with 4-hydroxy-1-methylpiperidine or 2-(4-phenyl-piperazino)-ethanol can be carried out in conventional manner in the presence or absence of an additional solvent and/or of a dehydrating agent. Suitable solvents include for example, hydrocarbons, e.g., benzene, toluene or xylene, halogenated hydrocarbons, e.g., methylene chloride, chloroform or 1,2-dichloroethane, and ethers, e.g., tetrahydrofuran. Substances which have proved suitable as dehydrating agents are, in particular, carbodiimides, e.g., dicyclohexylcarbodiimide. The esterification is preferably carried out at temperatures of approximately 0° to approximately 140° C.; as a rule it has ended after 30 minutes to 8 hours.

A reaction of the carboxylic acids III or of their reactive derivatives, especially their chlorides, with o-aminophenol or o-amino-thiophenol is carried out by the customary methods for benzoxazole or benzthiazole syntheses. If the free acids III are used as the starting materials, the reaction is preferably carried out in the presence of a dehydrating agent, e.g., $P_2O_5$ or polyphosphoric acid; if the chlorides are used, it is advantageous to add a base in order to bind the hydrogen chloride formed, for example dimethylaniline or pyridine, which at the same time can serve as solvents. For these reactions, the reaction temperatures are preferably approximately 20° to approximately 200° C., and preferentially 100° to 180° C. The reaction times are as a rule approximately 30 minutes to 8 hours.

Tetrazoles of formula I ($R^2$=tetrazol-5-yl) are preferably obtainable by reacting a nitrile of formula V, or a reactive derivative thereof, for example a corresponding imido-ester, with hydrazoic acid or one of its salts, preferably one of its alkali metal salts, e.g., sodium azide. The nitriles of formula V and the corresponding imido-esters are either known of can be prepared from known compounds with the aid of known methods. The reaction preferably proceeds in the presence of one of the aforementioned solvents. Dimethylformamide is the preferred solvent. The reaction temperatures are preferably approximately 20° to approximately 200° and preferentially 80° to 150° C. The imidoesters are preferably reacted with free hydrazoic acid in benzene at the boil. For these reactions, the reaction times are as a rule 1 hour to 10 days.

Compounds of formula I in which $R^2$ is a tetrazol-5-yl group are also obtainable in good yields by reacting amidrazones of the formula VI, which, in turn, are readily obtainable from the corresponding nitriles and sodium hydrazide, with nitrous acid or one of its salts, preferably one of its alkali metal salts, e.g., sodium nitrite. This reaction proceeds, for example, in aqueous-alcoholic, for example, aqueous-ethanolic, solution at temperatures of approximately −10° to +20° C. and preferably 0° to 5° C. Preferably, an aqueous solution of sodium nitrite is added dropwise to an acidified alcoholic solution of the amidrazone and the reaction mixture is then left to stand at 0° to 5° C. for about 1 to 48 hours.

The reaction of aldehydes of the formula VII with aminothiols of the formula VIII results in compounds of the formula I in which $R^2$ is benzthiazol-2-yl or 3—R$^3$—4—R$^4$—thiazolidin-2-yl, the reaction being carried out in the presence of an oxidizing agent in the former case. The aldehydes of the formula VII are easily obtainable by reduction of the corresponding carboxylic acids of the formula III or of their esters or by oxidation of the corresponding alcohols of the formula R—CH$_2$OH, which, in turn, are obtainable by reduction of the acids or of the esters. The aminothiols of the formula VIII are either known or can be prepared from known starting materials by known methods. In place of the starting materials VII and VIII, it is also possible to use corresponding reactive derivatives, for example the acetals, hemithioacetals, thioacetals, acylals or thioacylals corresponding to VII and the mercaptides, especially the alkali metal mercaptides, of VIII. The reaction of VII with VIII is preferably carried out in the presence of an inert solvent, for example of one of the abovementioned solvents; the reaction to produce the thiazolidines is carried out particularly advantageously in aqueous-alcoholic, for example aqueous-ethanolic, weakly acid solution at temperatures of approximately 0° to approximately 80° and preferably of 15° to 30° C.; the reaction to produce the benzthiazoles is carried out in a hydrocarbon, such as benzene or toluene, in the presence of an acid catalyst, e.g., hydrochloric acid, sulfuric acid or p-toluenesulfonic acid, with the admission of air, at temperatures of approximately 50° to approximately 150° and preferably of 80° to 110° C. In the latter case, the presence of an oxidizing agent is required, but as a rule the admission of air or the introduction of oxygen suffices.

Compounds of formula I in which $R^2$ is 3—acyl—4—R$^4$—thiazolidin-2-yl are also obtainable by conventional N-acylation of the corresponding NH compound (I, $R^2$=4—R$^4$—thiazolidin-2-yl). Suitable acylating agents include preferably the halides (for example chlorides or bromides) or anhydrides of carboxylic acids with 1-7 C atoms, for example acetic anhydride, propionyl chloride, isobutyryl bromide, formic acid/acetic acid anhydride or benzoyl chloride. The addition of a base, such as pyridine or triethylamine, during the acylation is possible but not necessary. The acylation is preferably carried out in the presence or absence of one of the inert solvents mentioned, for example benzene, at temperatures of approximately 0° to approximately 160° C. and preferably approximately 20° to approximately 120° C. The mentioned base, for example pyridine, or an excess of the acylating agent can also serve as solvents.

A base of formula I can be converted by means of an acid to the corresponding acid addition salt. Acids which can be used for this reaction are those which produce physiologically acceptable salts. Thus, it is possible to use inorganic acids, for example sulfuric acid, nitric acid, hydrogen halide acids, e.g., hydrochloric acid or hydrobromic acid, or phosphoric acids, e.g., orthophosphoric acid, and also organic acids, especially aliphatic, alicyclic, araliphatic, aromatic or heterocyclic monobasic or polybasic carboxylic, sulfonic or sulfuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-mono- and -di-sulfonic acids and laurylsulfuric acid.

The acids of formula I ($R^4$=COOH) can be converted by reaction with a base to one of their physiologically acceptable metal or ammonium salts. Suitable salts include, in particular, the sodium, potassium, magnesium, calcium and ammonium salts, and also substituted ammonium salts, for example the dimethyl-, diethyl- and diisopropylammonium, monoethanol-, diethanol- and triethanol-ammonium, cyclohexylammonium, dicyclohexylammonium and dibenzylethylene diammonium salts.

The present invention also relates to the use of the compounds of formula I and their physiolgocially acceptable salts for the preparation of pharmaceutical formulations, especially by a non-chemical route. The mentioned compounds can be brought into a suitable dosage form together with at least one solid, liquid and/or semi-liquid excipient or auxiliary and, if desired, in combination with one or more additional active substances.

It has been found that the compounds of formula I possess valuable pharmacological properties coupled with good tolerance. In particular, analgesic effects are found and these can be demonstrated in mice, for example in the pain test (writhing test) by the method of Siegmund et al. (Proc. Soc. Exp. Biol. (N.Y.) 95, (1957), pages 729–731.) Furthermore, for example, effects which lower the cholesterol level and the triglyceride level are also shown and can be demonstrated in the serum of rats by the method of Levine et al. (Automation in Analytical Chemistry, Technicon Symposium 1967, Mediad, New York, pages 25–28) and by the method of Noble and Campbell (Clin. Chem. 16 (1970), pages 166-170). It is also possible to observe antiphlogistic effects (which can be demonstrated, for example, on rats by the method of Winter et al, Proc. Soc. Exp. Biol. (N.Y.) 111, (1962), page 544) and also enzyme-inducing, fibrinolytic and thrombocyte aggregation-inhibiting effects by the methods customary for this purpose.

The compounds of formula I can therefore be used as medicinally active substances in human medicine and veterinary medicine. Furthermore, they can be used as intermediate products for the preparation of other medicinally active substances.

Thus, the present invention also relates to agents, especially pharmaceutical formulations, containing at least one compound of formula I and/or one physiologically acceptable salt thereof.

These formulations can be used as medicaments for patients in human medicine or veterinary medicine. Excipients which can be used include organic or inorganic substances which are suitable for enteral (for example oral) or parenteral administration or topical application and do not react with the new compounds, for example water, vegetable oils, benzyl alcohols, polyethylene glycols, glycerol triacetate, gelatine, carbohydrates, such as lactose or starch, magnesium stearate, talc or white petroleum jelly. Formulations for oral use include in particular tablets, sugar-coated tablets, capsules, syrups, juices or drops, for rectal use include suppositories, for parenteral use include solutions, preferably oily or aqueous solutions, and also suspensions, emulsions or implants, and for topical use include ointments, creams or powders. If the medicaments are to be administered in the form of powders in measured amounts, the packaging materials, such as paper sachets or paper capsules, are also suitable excipients. The new compounds can also be lyophilized and the resulting lyophilizates can be used, for example, to prepare injection preparations. The indicated formulations can be sterilized and/or contain auxiliaries, such as lubricants, preservatives, stabilizers and/or wetting agents, emulsifiers, salts for influencing the osmotic pressure, buffer substances, dyes, flavorings and/or aroma generating substances. If desired, they can also contain one or more additional active substances, for example one or more vitamins.

The present invention also relates to the use of the compounds of formula I in combating diseases, especially painful diseases of the locomotor system (rheumatism), and pain in other organs, and also to their use in the therapeutic treatment of the human or animal body.

The substances according to this invention are as a rule administered analogously to known, commercially available analgesics or antiphlogistic agents (for example metamizole, acetylsalicylic acid and paracetamol), preferably in dosages of approximately 1 to 500 mg and especially 5 to 50 mg per dosage unit. The daily dose is preferably approximately 0.02 to 10 mg/kg of body weight. The particular dose for each specific patient depends, however, on the usual very diverse factors, for example on the effectiveness of the particular compound employed; on the age, body weight, general state of health, sex and diet of the patient; on the time and route of administration; on the rate of excretion; on the medicinal combination; and on the severity of the particular disease to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Each of the compounds of formula I named in the examples which follow is particularly suitable for the preparation of pharmaceutical formulations.

In the examples which follow, "customary working up" refers to the following method:

Water is added if necessary; the reaction mixture is extracted with an organic solvent, e.g., benzene, chloroform or methylene chloride; the phases are separated; the organic phase is dried over sodium sulfate and filtered; the filtrate is evaporated; and the product is purified by chromatography and/or crystallization.

EXAMPLE 1

A mixture of 33.8 g of 1-methyl-4-piperidyl 3-p-chlorobenzoyl-3-formyl-propionate [obtainable by esterification of 3-p-chlorobenzoylpropionic acid with 4-hydroxy-1-methylpiperidine to produce 1-methyl-4-piperidyl-3-p-chlorobenzoylpropionate and a subsequent condensation reaction of the latter with ethyl formate], 11.9 g of phenylhydrazine, 7 ml of acetic acid and 350 ml of ethanol is boiled for 2 hours and then evaporated. After the customary working up, 1-methyl-4-piperidyl (5-p-chlorophenyl-1-phenyl-pyrazol-4-yl)-acetate is obtained; m.p. 90°–93°. Hydrochloride, m.p. 234°–236°.

EXAMPLES 2 TO 16

Analogously to Example 1,
2. 2-(4-Phenylpiperazino)-ethyl (5-p-chlorophenyl-1-phenyl-pyrazol-4-yl)-acetate, m.p. 78°–80°. Hemisuccinate (acid succinate), m.p. 105°–107°,
3. 5-p-Chlorophenyl-1-phenyl-4-(benzoxazol-2-ylmethyl)-pyrazole, m.p. 137°–139°,
4. 5-p-Chlorophenyl-1-phenyl-4-(benzthiazol-2-ylmethyl)-pyrazole, m.p. 135°–137°.
5. 5-p-Chlorophenyl-1-phenyl-4-(tetrazol-5-ylmethyl)-pyrazole, m.p. 230°–232°,
6. 5-p-Chlorophenyl-1-phenyl-4-(thiazolidin-2-ylmethyl)-pyrazole, m.p. 147°–148°. Dihydrochloride, m.p. 173°–176°. Phosphate, m.p. 170°–172°.
7. 5-p-Chlorophenyl-1-phenyl-4-(4-carboxythiazolidin-2-ylmethyl)-pyrazole, m.p. 175°–177°.
8. 4-(3-Acetylthiazolidin-2-ylmethyl)-5-p-chlorophenyl-1-phenyl-pyrazole, m.p. 121°–122°,
9. 1-Methyl-4-piperidyl (1,5-diphenyl-pyrazol-4-yl)-acetate,
10. 2-(4-Phenylpiperazino)-ethyl (1,5-diphenyl-pyrazol-4-yl)-acetate,
11. 1,5-Diphenyl-4-(benzoxazol-2-ylmethyl)-pyrazole,
12. 1,5-Diphenyl-4-(benzthiazol-2-ylmethyl)-pyrazole,
13. 1,5-Diphenyl-4-(tetrazol-5-ylmethyl)-pyrazole,
14. 1,5-Diphenyl-4-(thiazolidin-2-ylmethyl)-pyrazole,
15. 1,5-Diphenyl-4-(4-carboxythiazolidin-2-ylmethyl)-pyrazole and
16. 4-(3-Acetylthiazolidin-2-ylmethyl)-1,5-diphenyl-pyrazole
are obtained from
2-(4-phenylpiperazino)-ethyl 3-p-chlorobenzoyl-3-formylpropionate,
2-(2-p-chlorobenzoyl-3-oxopropyl)-benzoxazole,
2-(2-p-chlorobenzoyl-3-oxopropyl)-benzthiazole,
5-(2-p-chlorobenzoyl-3-oxopropyl)-tetrazole,
2-(2-p-chlorobenzoyl-3-oxopropyl)-thiazolidine,
2-(2-p-chlorobenzoyl-3-oxopropyl)-thiazolidine-4-carboxylic acid,
2-(2-p-chlorobenzoyl-3-oxopropyl)-3-acetyl-thiazolidine,
1-methyl-4-piperidyl 3-benzoyl-3-formyl-propionate and
2-(4-phenylpiperazino)-ethyl 3-benzoyl-3-formyl-propionate,
2-(2-benzoyl-3-oxopropyl)-benzoxazole,
2-(2-benzoyl-3-oxopropyl)-benzthiazole,
5-(2-benzoyl-3-oxopropyl)-tetrazole,
2-(2-benzoyl-3-oxopropyl)-thiazolidine,
2-(2-benzoyl-3-oxopropyl)-thiazolidine-4-carboxylic acid and
2-(2-benzoyl-3-oxopropyl)-3-acetyl-thiazolidine respectively, with phenylhydrazine.

EXAMPLE 17

35.1 g of 1-methyl-4-piperidyl 3-p-chlorobenzoyl-4-dimethylamino-3-butenoate [obtainable by esterification of 3-p-chlorobenzoyl-propionic acid with 1-methylpiperidin-4-ol to produce 1-methyl-4-piperidyl 3-p-chloro-benzoylpropionate and subsequent reaction of the latter with dimethylformamide dimethyl acetal in the presence of acetic acid at 120°] and 12 g of phenylhydrazine are warmed for 4 hours at 100°. The reaction mixture is subjected to the customary working up (benzene/water) and 1-methyl-4-piperidyl 5-p-chlorophenyl-1-phenyl-pyrazol-4-yl-acetate is obtained; m.p. 90°–93°. Hydrochloride, m.p. 234°–235°.

EXAMPLES 18 TO 20

Analogously to Example 17,
18. 2-(4-Phenylpiperazino)-ethyl (5-p-chlorophenyl-1-phenyl-pyrazol-4-yl)-acetate, m.p. 78°–80°; hemisuccinate, m.p. 105°–107°,
19. 1-Methyl-4-piperidyl (1,5-diphenyl-pyrazol-4-yl)-acetate and
20. 2-(4-Phenylpiperazino)-ethyl (1,5-diphenyl-pyrazol-4-yl)-acetate
are obtained from
2-(4-phenylpiperazino)-ethyl 3-p-chlorobenzoyl-4-dimethylamino-3-butenoate,
1-methyl-4-piperidyl 3-benzoyl-4-dimethylamino-3-butenoate and
2-(4-phenylpiperazino)-ethyl 3-benzoyl-4-dimethylamino-3-butenoate respectively, with phenylhydrazine.

EXAMPLE 21

A solution of 2.27 g of dicyclohexylcarbodiimide in 10 ml of dry THF is added slowly, at 5°–10°, to a solution of 3.13 g of (5-p-chlorophenyl-1-phenyl-pyrazol-4-yl)-acetic acid in 25 ml of dry THF. The mixture is stirred for 15 minutes at 5°–10°, a solution of 1.23 g of 4-hydroxy-1-methylpiperidine in 10 ml of dry THF is then added at 5°–10°, the resulting mixture is stirred for 3 hours at 20° and subjected to the customary working up, and 1-methyl-4-piperidyl (5-p-chlorophenyl-1-phenylpyrazol-4-yl)-acetate is obtained; m.p. 90°–93°. Hydrochloride, m.p. 234°–236°.

EXAMPLES 22 TO 24

Analogously to Example 21,
22. 2-(4-Phenylpiperazino)-ethyl (5-p-chlorophenyl-1-phenyl-pyrazol-4-yl)-acetate, m.p. 78°–80°; hemisuccinate, m.p. 106°–107°,
23. 1-Methyl-4-piperidyl (1,5-diphenyl-pyrazol-4-yl)-acetate and
24. 2-(4-Phenyl-piperazino)-ethyl (1,5-diphenyl-pyrazol-4-yl)-acetate
are obtained from (5-p-chlorophenyl-1-phenylpyrazol-4-yl)-acetic acid or from (1,5-diphenyl-pyrazol-4-yl)-acetic acid with 2-(4-phenylpiperazino)-ethanol or 4-hydroxy-1-methylpiperidine.

EXAMPLE 25

A mixture of 10.9 g of o-aminophenol, 33.1 g of (5-p-chlorophenyl-1-phenyl-pyrazol-4-yl)-acetyl chloride and 100 ml of dimethylaniline is heated for 1 hour at 100° and then for 1 hour at 160°. The mixture is cooled and subjected to the customary working up and 5-p-chlorophenyl-1-phenyl-4-(benzoxazol-2-ylmethyl)-pyrazole is obtained; m.p. 137°–139°.

EXAMPLE 26

1,5-Diphenyl-4-(benzoxazol-2-ylmethyl)-pyrazole is obtained analogously to Example 25 using (1,5-diphenylpyrazol-4-yl)-acetyl chloride.

EXAMPLE 27

A mixture of 31.3 g of (5-p-chlorophenyl-1-phenyl-pyrazol-4-yl)-acetic acid, 10.9 g of o-aminophenol and 400 ml of polyphosphoric acid is heated at 175° for 2 hours. After cooling and the customary working up, 5-p-chlorophenyl-1-phenyl-4-(benzoxazol-2-ylmethyl)-pyrazole is obtained; m.p. 137°–139°.

EXAMPLE 28

1,5-Diphenyl-4-(benzoxazol-2-ylmethyl)-pyrazole is obtained analogously to Example 27 using (1,5-diphenyl-pyrazol-4-yl)-acetic acid.

EXAMPLE 29

A mixture of 12.5 g of 2-amino-thiophenol, 33.1 g of (5-p-chlorophenyl-1-phenyl-pyrazol-4-yl)-acetyl chloride and 100 ml of dimethylaniline is heated for 1 hour at 100° and then for 1 hour at 140°. The mixture is cooled and subjected to the customary working up and 5-p-chlorophenyl-1-phenyl-4-(benzthiazol-2-ylmethyl)-pyrazole is obtained; m.p. 135°–137°.

EXAMPLE 30

1,5-Diphenyl-4-(benzthiazol-2-ylmethyl)-pyrazole is obtained analogously to Example 29 using (1,5-diphenylpyrazol-4-yl)-acetyl chloride.

EXAMPLE 31

A mixture of 29.4 g of (5-p-chlorophenyl-1-phenyl-pyrazol-4-yl)-acetonitrile, 8.06 g of sodium azide, 6.64 g of NH$_4$Cl and 140 ml of dry DMF is heated at 120° for 17 hours, with stirring, and is then evaporated. After the customary working up, 5-p-chlorophenyl-1-phenyl-4-(tetrazol-5-ylmethyl)-pyrazole is obtained; m.p. 230°–232°.

EXAMPLE 32

1,5-Diphenyl-4-(tetrazol-5-ylmethyl)-pyrazole is obtained analogously to Example 31 using (1,5-diphenyl-pyrazol-4-yl)-acetonitrile.

EXAMPLE 33

34 g of imidoethyl (5-p-chlorophenyl-1-phenyl-pyrazol-4-yl)-acetate are boiled with 120 ml of a solution of 0.15 mol of hydrazoic acid in benzene for 2 hours. A further 40 ml of the hydrazoic acid solution are then added (the total amount is thus 0.2 mole). The mixture is boiled for a further 2 hours, cooled and subjected to the customary working up and 5-p-chlorophenyl-1-phenyl-4-(tetrazol-5-ylmethyl)-pyrazole is obtained; m.p. 230°–232°.

EXAMPLE 34

A solution of 0.75 g of NaNO$_2$ in 10 ml of water is added dropwise to a solution of 3.26 g of 5-p-chlorophenyl-1-phenyl-pyrazol-4-yl-acetic acid amidrazone (obtainable from the nitrile and sodium hydrazide) in 250 ml of ethanol and 3 g of 38% hydrochloric acid. The mixture is left to stand for 24 hours at 0°, neutralized with sodium hydroxide solution, evaporated and subjected to the customary working up and 5-p-chlorophenyl-1-phenyl-4-(tetrazol-5-ylmethyl)-pyrazole is obtained; m.p. 230°–232°.

EXAMPLE 35

A mixture of 29.7 g of (5-p-chlorophenyl-1-phenyl-pyrazol-4-yl)-acetaldehyde [m.p. 130°–132°; obtainable by reduction of ethyl (5-p-chlorophenyl-1-phenyl-pyrazol-4-yl)-acetate with LiAlH₄ to give 5-p-chlorophenyl-4-(2-hydroxyethyl)-1-phenylpyrazole (m.p. 120°–122°) and oxidation of the latter with dimethylsulfoxide/dicyclohexylcarbodiimide in benzene at 25°], 13.5 g of cysteamine hydrochloride, 8.67 g of CH₃COOK, 75 ml of water and 150 ml of ethanol is stirred at 25° for 2 hours. It is subjected to the customary working up (water/ethyl acetate) and 5-p-chlorophenyl-1-phenyl-4-(thiazolidin-2-yl-methyl)-pyrazole is obtained; m.p. 147°–148°. Dihydrochloride, m.p. 173°–176°. Phosphate, m.p. 170°–172°.

EXAMPLE 36

1,5-Diphenyl-4-(thiazolidin-2-ylmethyl)-pyrazole is obtained analogously to Example 35 using (1,5-diphenylpyrazol-4-yl)-acetaldehyde.

EXAMPLES 37 AND 38

Analogously to Examples 35 and 36,
37. 5-p-Chlorophenyl-1-phenyl-4-(4-carboxythiazolidin-2-ylmethyl)-pyrazole, m.p. 175°–177°, and
38. 1,5-Diphenyl-4-(4-carboxythiazolidin-2-ylmethyl)-pyrazole
are obtained using cysteine hydrochloride.

EXAMPLE 39

A mixture of 29.7 g of (5-p-chlorophenyl-1-phenyl-pyrazol-4-yl)-acetaldehyde, 12.5 g of 2-aminothiophenol, 18 g of p-toluenesulfonic acid and 500 ml of toluene is boiled for 3 hours under a water separator, air having access to the mixture.

The customary working up gives 5-p-chlorophenyl-1-phenyl-4-(benzthiazol-2-ylmethyl)-pyrazole, m.p. 135°–137°.

EXAMPLE 40

A mixture of 3.56 g of 5-p-chlorophenyl-1-phenyl-4-(thiazolidin-2-yl-methyl)-pyrazole and 55 ml of acetic anhydride is boiled for 3 hours. 55 ml of pyridine is then added and the mixture is heated for a further 5 hours at 50° and subjected to the customary working up. 4-(3-Acetylthiazolidin-2-yl-methyl)-5-p-chlorophenyl-1-phenylpyrazole is obtained; m.p. 121°–122°.

EXAMPLES 41 TO 47

Analogously to Example 40,
41. 4-(3-Propionyl-thiazolidin-2-ylmethyl)-5-p-chlorophenyl-1-phenylpyrazole,
42. 4-(3-Butyryl-thiazolidin-2-ylmethyl)-5-p-chlorophenyl-1-phenylpyrazole,
43. 4-(3-Isobutyryl-thiazolidin-2-ylmethyl)-5-p-chlorophenyl-1-phenylpyrazole,
44. 4-(3-Valeryl-thiazolidin-2-ylmethyl)-5-p-chlorophenyl-1-phenylpyrazole,
45. 4-(3-Hexanoyl-thiazolidin-2-ylmethyl)-5-p-chlorophenyl-1-phenylpyrazole,
46. 4-(3-Heptanoyl-thiazolidin-2-ylmethyl)-5-p-chlorophenyl-1-phenylpyrazole and
47. 4-(3-Benzoyl-thiazolidin-2-ylmethyl)-5-p-chlorophenyl-1-phenylpyrazole
are obtained using the corresponding acid anhydrides.

EXAMPLES 48 TO 55

Analogously to Example 40 to 47,
48. 4-(3-Acetyl-thiazolidin-2-ylmethyl)-1,5-diphenylpyrazole,
49. 4-(3-Propionyl-thiazolidin-2-ylmethyl)-1,5-diphenylpyrazole,
50. 4-(3-Butyryl-thiazolidin-2-ylmethyl)-1,5-diphenylpyrazole,
51. 4-(3-Isobutyryl-thiazolidin-2-ylmethyl)-1,5-diphenylpyrazole,
52. 4-(3-Valeryl-thiazolidin-2-ylmethyl)-1,5-diphenylpyrazole,
53. 4-(3-Hexanoyl-thiazolidin-2-ylmethyl)-1,5-diphenylpyrazole,
54. 4-(3-Heptanoyl-thiazolidin-2-ylmethyl)-1,5-diphenylpyrazole and
55. 4-(3-Benzoyl-thiazolidin-2-ylmethyl)-1,5-diphenylpyrazole
are obtained from 1,5-diphenyl-4-(thiazolidin-2-ylmethyl)-pyrazole.

The following examples relate to pharmaceutical formulations which contain pyrazole derivatives of formula I or their salts.

EXAMPLE A: Tablets

A mixture of 1 kg of 5-p-chlorophenyl-1-phenyl-4-(thiazolidin-2-yl-methyl)-pyrazole dihydrochloride, 4 kg of lactose, 1.2 kg of potato starch, 0.2 kg of talc and 0.1 kg of magnesium stearate is compressed into tablets in a conventional manner, in such a way that each tablet contains 50 mg of active substance.

EXAMPLE B: Sugar-coated tablets

Tablets are compressed analogously to Example A. These are then coated in a conventional manner with a coating of sucrose, potato starch, talc, tragacanth and dye.

EXAMPLE C: Capsules 10 kg of the hydrochloride of 1-methyl-4-piperidyl 5-p-chlorophenyl-1-phenyl-pyrazol-4-yl-acetate are filled in a conventional manner into hard gelatine capsules so that each capsule contains 50 mg of active substance.

EXAMPLE D: Ampoules

A solution of 1 kg of the hemisuccinate of 2-(4-phenylpiperazino)-ethyl 5-p-chlorophenyl-1-phenyl-pyrazol-4-yl-acetate in 30 l of twice-distilled water is subjected to sterile filtration, filled into ampoules and lyophilized under sterile conditions. The ampoules are sealed under sterile conditions. Each ampoule contains 20 mg of active substance.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:
1. A pyrazole derivative of the formula

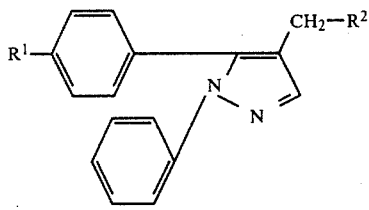

wherein R[1] is H or Cl; R[2] is 1-methyl-4-piperidyloxycarbonyl, 2-(4-phenylpiperazino)-ethoxycarbonyl, benzoxazol-2-yl, benzthiazol-2-yl, tetrazol-5-yl or 3-R[3]-4-R[4]-thiazolidin-2-yl; R[3] is H, alkanoyl of 1–7 C atoms or benzoyl; and R[4] is H or COOH, or a physiologically acceptable salt thereof.

2. A compound of claim 1 wherein R[1] is Cl.

3. A compound of claim 1 wherein R[2] is 1-methyl-4-piperidyl-oxycarbonyl or 2-(4-phenyl-piperazino)-ethoxycarbonyl.

4. A compound of claim 1 wherein R[1] is Cl and R[2] is 1-methyl-4-piperidyl-oxycarbonyl or 2-(4-phenyl-piperazino)-ethoxycarbonyl.

5. 1-Methyl-4-piperidyl 5-p-chlorophenyl-1-phenyl-pyrazol-4-yl-acetate;

2-(4-Phenylpiperazino)-ethyl 5-p-chlorophenyl-1-phenyl-pyrazol-4-yl-acetate;

5-p-Chlorophenyl-1-phenyl-4-(tetrazol-5-ylmethyl)-pyrazole; or 5-p-Chlorophenyl-1-phenyl-4-(thiazolidin-2-ylmethyl)-pyrazole, compounds of claim 1.

6. A pharmaceutical composition comprising an analgesically effective amount of a compound of claim 1 and a pharmaceutically acceptable carrier.

7. A pharmaceutical composition comprising 1–500 mg of a compound of claim 1 and a pharmaceutically acceptable carrier.

8. A method of relieving pain in a patient which comprises administering an analgesically effective amount of a compound of claim 1 to the patient.

* * * * *